(12) United States Patent
Remmert et al.

(10) Patent No.: US 10,737,091 B2
(45) Date of Patent: Aug. 11, 2020

(54) ELECTRODE AND ELECTRODE PAD FOR THE ELECTRICAL STIMULATION OF BRAIN TISSUE OR OTHER TISSUE OF A PATIENT

(71) Applicant: Precisis AG, Heidelberg (DE)

(72) Inventors: Gregor Remmert, Heidelberg (DE); Stefan Menzl, Jona/SG (CH)

(73) Assignee: PRECISIS AG, Heidelberg (DE)

( * ) Notice: Subject to any disclaimer, the term of this patent is extended or adjusted under 35 U.S.C. 154(b) by 97 days.

(21) Appl. No.: 15/726,821

(22) Filed: Oct. 6, 2017

(65) Prior Publication Data
US 2018/0117308 A1 May 3, 2018

Related U.S. Application Data

(60) Provisional application No. 62/415,537, filed on Nov. 1, 2016.

(51) Int. Cl.
| | | |
|---|---|---|
| *A61N 1/00* | (2006.01) | |
| *A61N 1/05* | (2006.01) | |
| *A61N 1/04* | (2006.01) | |
| *A61N 1/36* | (2006.01) | |
| *A61B 5/00* | (2006.01) | |
| *A61B 5/0478* | (2006.01) | |

(52) U.S. Cl.
CPC ......... *A61N 1/0534* (2013.01); *A61N 1/0424* (2013.01); *A61N 1/0456* (2013.01); *A61N 1/0529* (2013.01); *A61N 1/36067* (2013.01); *A61B 5/0478* (2013.01); *A61B 5/6868* (2013.01)

(58) Field of Classification Search
CPC .. A61N 1/0452; A61N 1/0456; A61N 1/0492; A61N 1/0526–1/0534; A61N 1/0424; A61N 1/36067; A61B 5/0478; A61B 5/6868
See application file for complete search history.

(56) References Cited

U.S. PATENT DOCUMENTS

| | | | |
|---|---|---|---|
| 8,024,049 B1 | 9/2011 | Gilson et al. | |
| 2002/0087201 A1 | 7/2002 | Firlik et al. | |
| 2003/0187490 A1* | 10/2003 | Gliner | A61N 1/0531 607/116 |
| 2006/0173510 A1 | 8/2006 | Besio et al. | |
| 2007/0238944 A1* | 10/2007 | Axelgaard | A61N 1/0452 600/372 |
| 2008/0147146 A1* | 6/2008 | Wahlgren | A61B 5/04001 607/61 |
| 2009/0112273 A1 | 4/2009 | Wingeier et al. | |
| 2011/0137381 A1* | 6/2011 | Lee | A61N 1/0529 607/62 |
| 2012/0203079 A1* | 8/2012 | McLaughlin | A61B 5/04012 600/301 |
| 2014/0214144 A1 | 7/2014 | Peterson et al. | |
| 2015/0065838 A1* | 3/2015 | Wingeier | A61B 5/0478 600/383 |
| 2016/0339239 A1* | 11/2016 | Yoo | A61N 1/36107 |
| 2016/0360990 A1* | 12/2016 | Altshuler | A61B 5/0478 |

\* cited by examiner

*Primary Examiner* — Scott M. Getzow
(74) *Attorney, Agent, or Firm* — W&C IP (57) ABSTRACT

An electrode for the electrical stimulation of brain tissue or other tissue of a patient is configured for location between skull and scalp of the patient. The electrode has a stimulation surface which is configured for contacting the skull of the patient. The electrode is a disc-shaped electrode having a pre-shaped flat or concave stimulation surface.

18 Claims, 6 Drawing Sheets

ELECTRODE AND ELECTRODE PAD FOR THE ELECTRICAL STIMULATION OF BRAIN TISSUE OR OTHER TISSUE OF A PATIENT

FIELD OF THE INVENTION

The present invention relates to the area of neurostimulation using electrical AC and/or DC stimulation pulses applied to a patient by means of electrodes.

Electrical stimulation of neural or nervous tissue, e.g., brain tissue, is a well-established procedure for the treatment of various neurological disorders. It has been successfully applied to treat diseases, such as Parkinson's disease, epilepsy, migraine, stroke, and many other neurological illnesses or conditions.

BACKGROUND

The established technologies are either highly invasive, e. g. by directly accessing the intracranial volume, or require stationary application. The disadvantage of non-invasive treatments of neurological disorders like tDCS or TMS is that they cannot be applied outside of the hospital setting due to the lack of accessible and safe mobile devices for therapeutic purposes. The disadvantage of the established intracranial neurostimulation systems (DBS or RNS) is their invasiveness and the associated risks for the patients.

A possibility for reducing the invasiveness of the treatment is to position the electrodes between skull and scalp of a patient. Such extracranial brain stimulation via electrodes located between skull and scalp face the challenge that the current must pass through the low conducting skull resulting in a resistance much larger for an extracranial stimulator compared to intracranial stimulation. The resistance seen by the stimulator can be up to 40 times larger than for a cortical stimulator with electrodes placed directly on the surface of the cortex. The exact magnitude of the resistance depends on the local thickness of the skull, its local conductivity, on the electrode contact area, and on the quality of the contact between electrode and skull.

There exists a need for optimized electrodes and electrode pads for efficient stimulation of the patient's tissue. A tight contact between the contact areas of the electrodes and the tissue of the patient, in particular to non-planar bone, is important for avoiding contact faults due to increased contact-resistance and increased leakage currents. So far, the electrodes proposed in the past are not optimum.

BRIEF SUMMARY OF THE INVENTION

The present invention overcomes all these disadvantages and restrictions by offering an electrode for the electrical stimulation of brain tissue or other tissue of a patient, the electrode being configured for location between skull and scalp of the patient, wherein the electrode has a stimulation surface which is configured for contacting the skull of the patient, wherein the electrode is a disc-shaped electrode having a pre-shaped flat or concave stimulation surface. In such a way, the stimulation surface of the electrode has a pre-shaped contour and shape which can optimally adapt to the outer shape of most areas of the skull of a human. The electrode is better adaptable to the curvature of the bone.

The inventors found that variables for reducing the resistance and hence the power consumption of the device are on the one hand an optimized electrode design in terms of shape, size, surface roughness, on the other hand process engineering solutions for an optimal electrical contact between the electrode and the skull and the prevention of shunt current losses.

The inventors found that current density distribution under the electrodes is a crucial factor to be considered when designing electrodes. The current density distribution under the electrodes can have a considerable effect on the electrochemical reactions at the electrode surface, thus affecting the corrosion behavior of the electrodes. It may cause in-tissue damage, impact the efficiency and agreeability of a therapy, and determine the power requirement of the device.

Attention must be paid to the fact that the current density distribution under electrodes is typically non-uniform. The so-called "edge-effect" describes an increase in current-density and subsequent enhancement of field-intensity towards the edge of an electrode. In case of disc-shaped electrodes, the current density distribution and the actual current density depend on the distance from the center of the electrode. 2D finite elements simulations indicate an increase of current density up to 5 times at the perimeter of smaller disc shaped electrodes. There are reports that patients undergoing electro-surgery sometimes suffer burns around the perimeter of the dispersive electrode, presumably due to high current and charge densities at the edge of the electrode. There is also evidence that the edge of cochlear implant electrodes are sometimes the preferred site for corrosion attacks. An optimal contact between the bone tissue and the high current density areas near the perimeter of the electrode is therefore crucial.

According to an advantageous embodiment of the invention the electrode is plane, cone-shaped or elsewise concavely shaped. The electrode can be made of a thin metal material. The electrode can for instance be cold-formed.

For brain stimulation via electrodes positioned on top of the cranium thin disc-type electrodes are well suited, preferentially made of Pt/Ir (Platinum-Iridium). The contact area of such electrodes is rather large (approximately 1 $cm^2$) to be able to deliver as high electric charges with the current pulses as possible. The curvature of the convex cranium surface however can vary significantly within the area of application. The electrode of the invention provides a tight contact between the contact area of the electrodes, namely the stimulation surface, and the bone tissue which is important.

According to an advantageous embodiment of the invention the electrode comprises at least one incision and/or cut-out, allowing the electrode to be more flexibly deformable for adaption to the outer shape of the skull of the patient. This allows an improved adaption of the stimulation surface of the electrode to the outer shape of the skull of the patient.

According to an advantageous embodiment of the invention the incision and/or cut-out
  a) generally runs in a radial direction of the disc-shape of the electrode, and/or
  b) generally runs in a circumferential direction of the disc-shape of the electrode, and/or
  c) generally runs in a spiral form.

According to feature a), an electrode having the appearance of a flower or a blossom can be realized. This allows for an improved adaption to the outer shape of the skull of the patient. The areas of the electrode which are divided by an incision can be pre-shaped in a way that such areas overlap one another. According to feature b), the electrode can be divided in several planes which can result in a terrace shape of the electrode.

According to an advantageous embodiment of the invention the electrode has a shape of a lily pad, an oxeye daisy flower and/or a terrace-like shape.

According to an advantageous embodiment of the invention the electrode comprises multiple electrode arms divided by cut-outs, wherein the electrode arms are joined at least one joining surface of the electrode.

According to an advantageous embodiment of the invention the incisions and/or cut-outs are without sharp edges, in particular with rounded outer curvature. In such a way, undesirable strong electrical fields and/or current density peaks are avoided. Also, injuries of the patient are avoided.

According to an advantageous embodiment of the invention the at least one joining surface is located in the center of the electrode.

According to an advantageous embodiment of the invention at least some of the multiple electrode arms are supported by a mechanical supporting structure located on a backside of the electrode which is opposite the stimulation surface side. This improves the mechanical robustness of the electrode while using very thin material for providing electrode.

According to an advantageous embodiment of the invention the electrode comprises at least one mounting hole, allowing mounting of the electrode to the skull of the patient by means of a mechanical fixation element guided through the at least one mounting hole. This allows for an easy and secure fixation of the electrode at the skull of the patient.

According to an advantageous embodiment of the invention the electrode is at least partially coated with a flexible material, in particular biocompatible elastomeric material like for instance ChronoPrene™, preferentially silicone. The elasticity of the flexible material allows relative movements so that the electrode can adapt to the shape of the bone. Further, the flexible material can provide electrical insulation on the backside of the electrode, which is opposite to the stimulation surface side.

According to an advantageous embodiment of the invention the diameter of the disc-shape of the electrode ranges from 10 to 20 millimeter. The current density pattern at the surface of an electrode depends on the electrode shape and size. The current density values increase for all types of electrodes with decreasing size of the electrode. The electric efficiency of planar and other disc electrodes can therefore be improved by high-perimeter design. Increasing the size of the electrodes lowers the resistance seen by the stimulator. However, to maintain the required level of current density in the cortex, it is necessary to align the injected current and the electrode diameter. Numerical 3-D simulations show that a minimum instantaneous power is needed with a diameter of a disc-shaped or other shaped electrode of 10 to 16 mm.

The disadvantages and restrictions of the prior art are further overcome by an electrode pad for the electrical stimulation of brain tissue or other tissue of a patient via electrodes located between skull and scalp of the patient, comprising one or more electrodes of the aforementioned type. By such an electrode pad, the aforementioned advantages can also be realized.

According to an advantageous embodiment of the invention the electrodes and/or leads for connecting the electrodes to a stimulating device are preassembled on a surgical mesh. This makes the electrode pad robust against shear forces, decreases its in-plane stretchability and thus reduces the risk of damaging leads or electrical contacts during handling. Further, the mesh provides a substrate for connective tissue of the patient that may penetrate the mesh at its parts that are not covered. This provides for additional fixation of the electrode pad at the patient.

Various different shapes of the mesh can be employed, such as ovals, squares and rectangles or any arbitrary shape. Various regular and irregular mesh grids can be thought of with various distances between grid lines. The mesh can be made of PET (polyethylene terephthalate).

According to an advantageous embodiment of the invention the surgical mesh is partially or totally embedded within or covered by a flexible pad, in particular a silicone pad. This further increases the robustness of the electrode pad.

According to an advantageous embodiment of the invention the electrode pad comprises at least one stimulation electrode and at least one secondary electrode. For example, the electrode pad can comprise a plurality of secondary electrodes, like two, three or preferentially four secondary electrodes.

According to an advantageous embodiment of the invention the stimulation electrode is or, if there are more than one stimulation electrode, the stimulation electrodes are located between a plurality of secondary electrodes. In such a way, a pseudo-laplacian electrode arrangement can be realized which provides for best current depths penetration of the stimulation pulses into the tissue of the patient.

The advantages are also realized by the use of an electrode or electrode pad of the aforementioned type for electrical stimulation of brain tissue or other tissue of a patient. The electrode or electrode pad can be used in an extracranial application, where the electrode or electrodes are located between skull and scalp of the patient.

The advantages are further realized by a method of applying an electrode, in particular an electrode of an electrode pad, e.g. an electrode pad of the aforementioned type, to the skull of a patient, wherein the electrode is located between skull and scalp of the patient and fixed to the skull via a mechanical fixation element and/or by chemical fixation means. The mechanical fixation can be done e.g. by screwing or stapling the electrode to the skull. The chemical fixation can be done e.g. by glueing the electrode to the skull. Especially glueing can be done preferentially on the outer circumference of the electrode, which supports the desired isolation effect. A fixation of the electrode by glueing has the additional advantage that an improved sealing of the electrode against the surrounding areas can be achieved. For this purpose, the glue may be located around the outer circumference of the electrode.

By such fixation the electrical contact of the electrode to the skull is improved, reducing the impedance. Further, an improved isolation of each electrode from the surrounding tissue and from the other electrodes can be realized, leading to lesser shunt effects and stronger and more focused stimulation of the target region of the patient.

According to an advantageous embodiment of the invention, the electrode is deformed when fixed to the skull from a pre-shaped form into a skull-specific form at the point of application on the patient.

So-called "Pseudo-Laplacian" electrode constellations with at least one central disc-shaped stimulation electrode surrounded by several discrete secondary disc-type electrodes is the constellation of choice for this type of stimulation for best current depth penetration. The electrode array consists of one central disc-type electrode and at least two, preferentially four secondary disc-type electrodes. The diameter of the central stimulation electrode ranges between 10 to 20 mm for minimum instantaneous power requirement of the device. In total, the stimulation electrode(s) and all secondary counter electrode(s) together shall have roughly the same effective area.

A tight contact between the contact areas of the electrodes and the non-planar bone is crucial to avoid contact faults due to increased contact-resistance and increased leakage currents. This is achieved via silicone coated, conductive electrodes. The electrodes and leads are pre-assembled on electrode pads, which are ready to use, safe, ease the implantation process, assure the exact position of each electrode, and adjust to the curvature of the cranium. This is achieved by fixing the electrodes and leads on a surgical mesh, which is partially embedded in a silicone pad and seals the electrodes against shunt losses.

The electrode pad is placed on top of the target area on the cranium and fixed to prevent later migration. Various methods of fixing the electrodes and/or the pad are possible (gluing, stapling, screwing, etc.). The preferred solution is to fix each electrode via a screw, preferentially a center screw onto the cranium as this improves the electrical contact over utilizing the contact pressure of the scalp only.

In case plane electrodes are used, fixed with a screw in their center, then it is advantageous if the electrodes are made of thin, rather flexible Pt/Ir foil. Non-plane, specially pre-shaped electrodes are preferred for electrode materials of sufficient stiffness.

For example, to be better adaptable to the curvature of the bone are silicone coated, cone-shaped electrodes can be used, comprising an incision which allows the electrode to adapt its shape better to the curvature of the cranium when fixed through a central screw. The cone shaped electrodes are made by cutting a sector out of a disc-shaped electrode. The electrode is subsequently formed into a cone until the cutting sites are contacting or overlapping each other and then coated with silicone. The elasticity of the silicone coating allows relative movements so that the cone can adapt to the shape of the substrate when fixed with a central screw without damaging the silicone coating.

BRIEF DESCRIPTION OF THE DRAWINGS

FIG. 1 system overview
FIG. 2 graphic representation of a neurostimulation system comprising electrodes on an electrode pad
FIGS. 3 to 9 several embodiments of electrodes of the invention both in plan view and sectional side view
FIGS. 10 to 11 an electrode pad in plan views from both sides.

DESCRIPTION OF THE INVENTION

The invention is now further explained in connection with a neurostimulation system where the electrode and electrode pad of the invention can be used.

The disclosed device is fully implantable and delivers stimulation to defined areas of the brain. It can be used for the treatment of various neurological disorders, amongst others refractory epilepsy, where the device prophylactically hinders the occurrence of epileptic seizures by delivering continuous stimulation pulses. A long-term stimulation enables changes in neuronal networks and plasticity to take place, so that a "modulation" effect occurs. Thus the brain will be less susceptible to epileptic seizures and the patient with epilepsy can live a higher quality of life.

Figure 1:
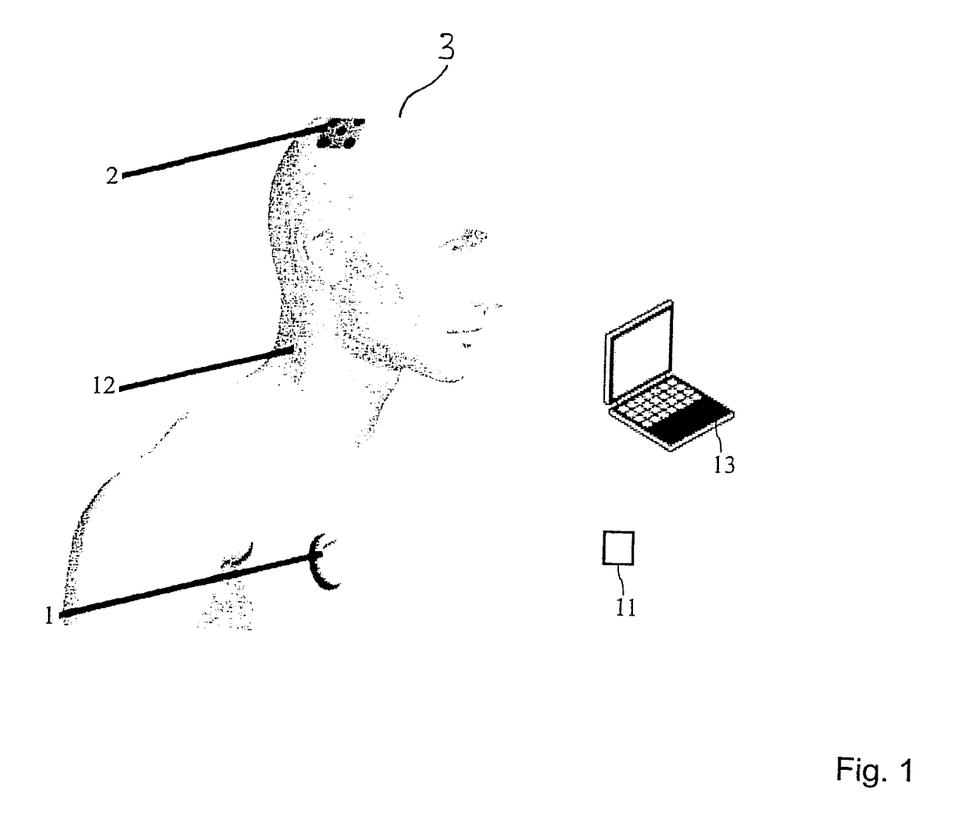

The system consists of three fully implantable parts and other accessory parts, as can be seen in FIG. 1:

A specialized electrode array 2, consisting of several electrodes assembled on a pad which is implanted in the subgaleal area (under the scalp but outside the skull). Each of these discrete, disc-type electrodes is individually controlled to create a symmetric electric field underneath the electrodes, which forces the current to travel perpendicular to the electrode surface and thus optimizes the penetration depth.

A power unit 1 containing a battery pack and the other elements including the stimulation/charge balancing control electronics is implanted below the clavicle.

A cable 12 linking the power unit 1 to the electrode array 2 is implanted under the skin.

A device 13 (not implanted) allows trained medical personnel to set the stimulation parameters according to the individual needs of the patient, as well as to test the functionality of the power supply unit (battery life, impedance) and provides access to data recorded by the patient (seizure log) consisting of a programming wand and a physician control center.

A handheld command device 11 (not implanted) enables the patient to record the event of a seizure, check the battery level, trigger the treatment with pre-set stimulation pulses, and turn the system off in case of an emergency.

Figure 2:
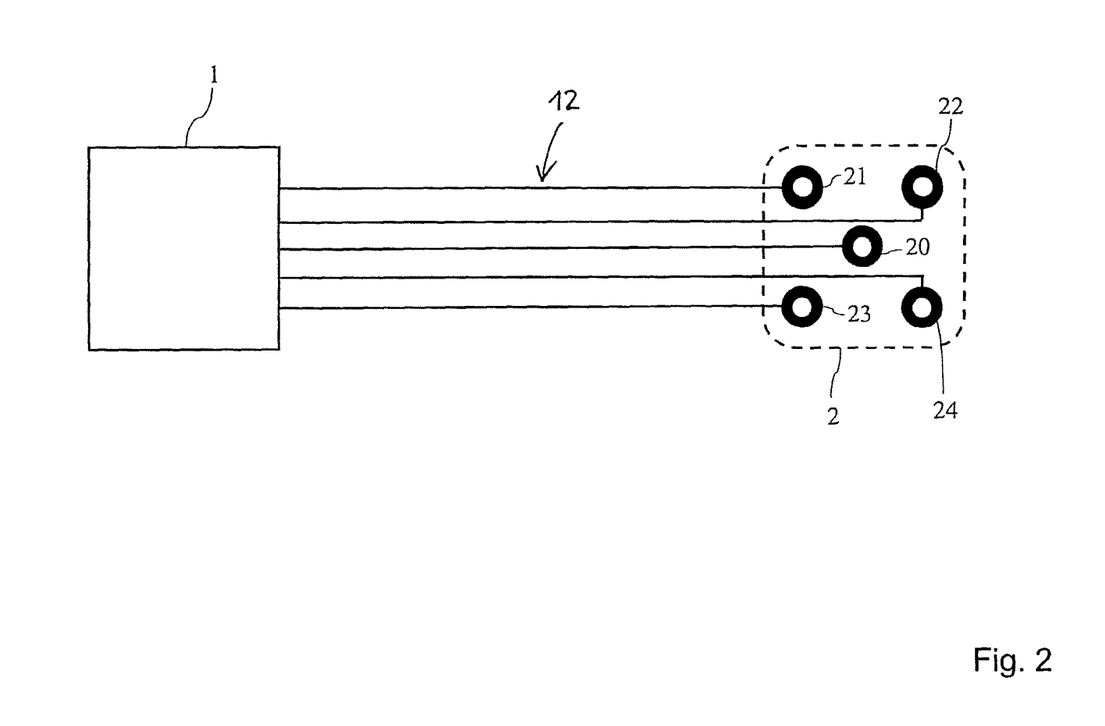

FIG. 2 shows a preferred pseudo-laplacian arrangement of the electrodes of the neurostimulation system. An electrode pad 2 comprises a stimulation electrode 20 and for secondary electrodes 21, 22, 23, 24. The stimulation electrode 20 can be located between the secondary electrodes, for example in the center of the electrode pad. Therefore, the secondary electrodes 21, 22, 23, 24 surround the stimulation electrode 20.

In FIGS. 3 to 9 the reference number 5 is generally used for the electrode. The electrode 5 can be any of the aforementioned electrodes 20, 21, 22, 23, 24. The basic principle of the present invention is that the electrode is pre-shaped, preferably with a concave stimulation surface, and having one or more incisions and/or cut outs, allowing the electrode to be more flexibly deformable and adaptable to the outer shape of the skull, and can be realized in several ways.

Figure 3:
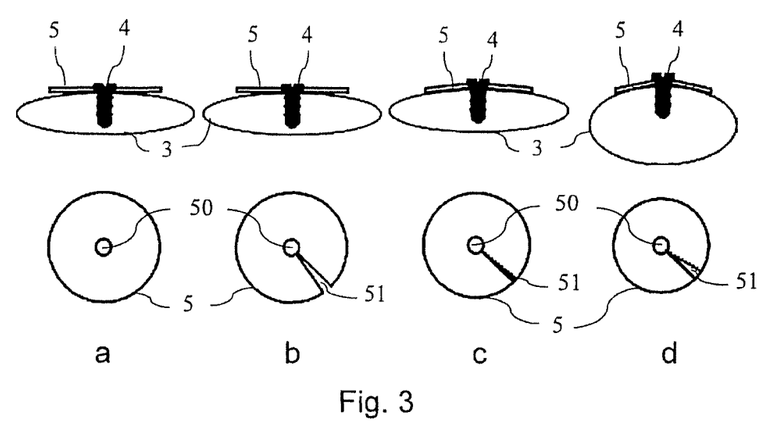

FIG. 3 shows four embodiments a) to d) of the inventive electrode. In the upper part of FIG. 3, sectional side views are depicted, in the lower part plan views on the backside of the electrode. As can be seen, the electrode can have a circular outer shape with an opening 50 in the center. The opening 50 can be used for fixation of the electrode 5 to the skull 3 by means of a screw 4. Embodiment a) is an electrode 5 with a plane shape, having a flat stimulation surface which is pressed by the screw 4 to the skull 3. Embodiment b) shows a similar electrode 5, but with a radially directed incision or cut-out 51. This allows for further improvement in the adaption of the shape of the stimulation surface to the shape of the skull 3 at the place of fixation. Embodiment c) shows an electrode comprising an incision 51. The electrode is pre-shaped with a concave stimulation surface. As can be seen, the adaption to the generally convex outer surface of the skull can be further improved because of the concave design of the stimulation surface. Embodiment d) shows the same electrode as embodiment c), but mounted to a region of the skull 3 with a smaller radius. As can be seen, the adaption of the shape of the stimulation surface to the outer shape of the skull 3 is improved also for such cases, making the electrode 5 of embodiments c) and d) a highly adaptable embodiment of the inventive electrode.

Figure 4:
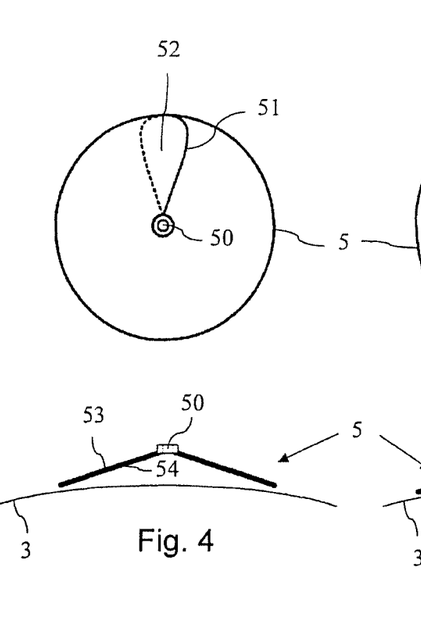
Figure 5:
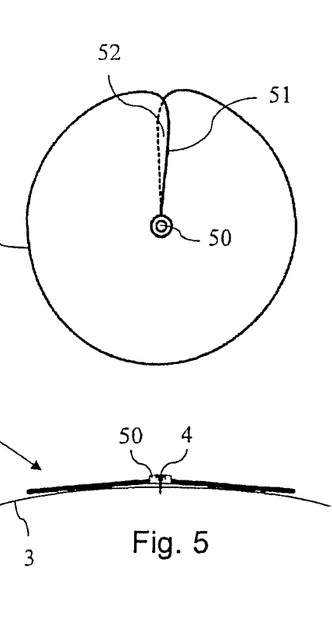

FIGS. 4 and 5 show a similar electrode like the one of embodiments c) and d) of FIG. 3. In contrast to embodiments c) and d) of FIG. 3, the incision is in this case not a linear incision, but an incision with a rounded curvature, without sharp edges at the location where the incision 51 merges into the circular outer shape of the electrode body. FIG. 4 shows the electrode 5 in a plan view on the backside (upper picture) and in a sectional side view near to the skull 3, before it is mounted to the skull 3. As can be seen in FIG. 4, the electrode is significantly more concave pre-shaped then the average convex outer shape of the skull 3. FIG. 5 shows the electrode of FIG. 4 when it is screwed to the skull. Due to the incision, the electrode can flexibly adapt to the outer shape of the skull 3 whereby the electrode 5 unfolded to a certain degree. This means that areas 52 of the electrode 5 which are overlapping each other are then reduced, as can be seen in the upper pictures of FIGS. 4 and 5. Due to this unfolding, the radius of the electrode 5 increases slightly.

The aforementioned exemplary embodiment of the inventive electrode can be prepared by cutting a segment out of a disc-shaped electrode such that no sharp edges are generated which may induce undesirable strong electrical fields and/or current density peaks. The form of such an electrode resembles a lily pad prior to bending.

Figure 6:
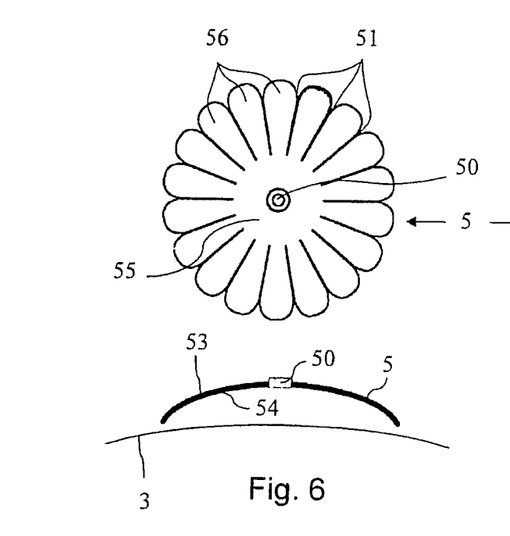
Figure 7:
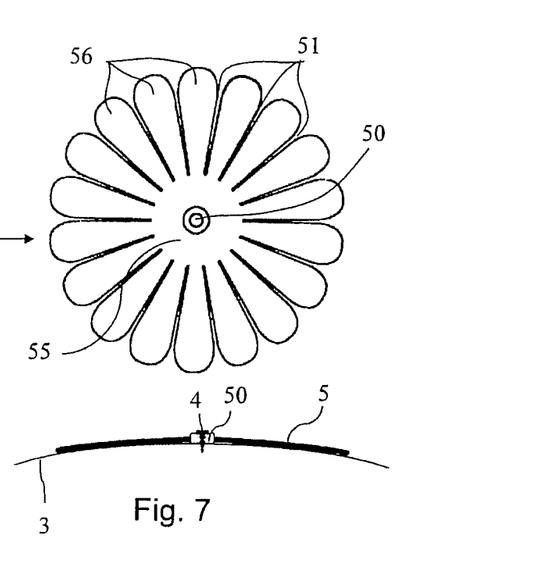

The electrode can also—prior or after pre-shaping—be segmented by multiple incisions 51 into multiple sections or lamellae 56, for instance through laser cutting, to overcome the challenges associated with pre-shaping a plane, disc type electrode to match the convex surface of a bone. An exemplary embodiment is shown in FIGS. 6 and 7. The individual segments 56 must have at least one joining surface 55, preferentially in the center of the electrode, where it is fixed, for instance by screwing.

FIGS. 6 and 7 show an electrode which has several radially directed incisions 51, which make the electrode look like an oxeye daisy flower. FIGS. 6 and 7 show the electrode in the upper picture in a plan view on the backside, and in the lower pictures in a sectional side view together with the skull 3. FIG. 6 shows the electrode before mounting to the skull, FIG. 7 shows the electrode mounted to the skull 3.

Figures 8, 9:
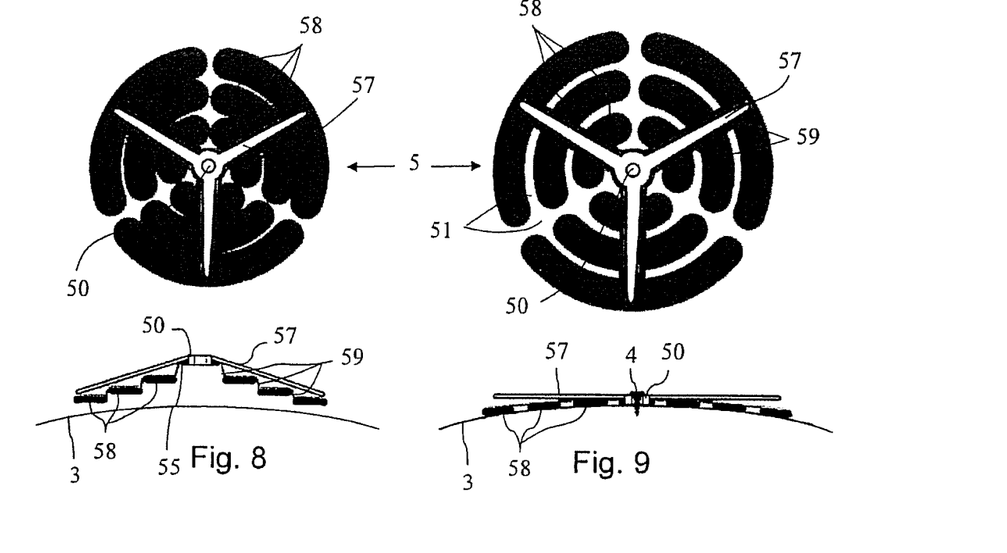
Figure 8A:
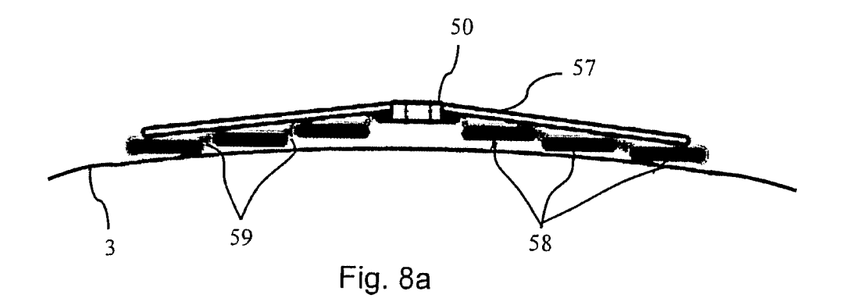

Another exemplary embodiment, depicted in FIGS. 8, 8a and 9, would be to segment a disc-type electrode 5 into several circular arcs 58 which are mechanically and electrically connected by radial connecting sections 59, and further supported by a mechanical supporting structure 57 located on the backside 53 of the electrode 5 which can be a finger-shaped device, which presses the terrace-like arranged arcs 58 onto the bone 3 during fixation, for instance by screwing.

In the embodiments of FIGS. 8, 8a and 9, the incisions 51 are a combination of three generally radially directed incisions 51 combined with three generally circumferentially directed incisions 51. In combination with the concave pre-shaped design of the electrode 5, the electrode 5 has the mentioned terrace-like shape with several stimulation lamellae established by the circular arcs 58 which get into contact with the skull 3 when fixed in place. The mechanical supporting structure 57 on the backside 53 supports the several electrode lamellae.

The terrace-like shaped electrode 5 according to FIGS. 8, 8a and 9 can be provided with several possible initial arrangements of the angles of the lamellae relative to each other. For example, it is possible, but not absolutely required that the lamellae are relative to each other in a concave arrangement. However, since the final position of the lamellae 58 is also controlled by the mechanical supporting structure 57, it is also possible to provide a terrace-like shaped electrode 5 where the lamellae 58 are initially in a convex arrangement relative to each other, with regard to the stimulation surface.

The mechanical supporting structure 57 can have a star-like shape, with three legs protruding from a center of the mechanical supporting structure 57, or with more than three legs. It is advantageous to provide the legs with equal angular spacing. In a top view, the legs may be located above bridging sections which mechanically connect the inner with the outer lamellae.

The mechanical supporting structure 57 both allows for fixating the electrode 5 to the skull 3 and for pressing and adapting the lamellae 58 to the convex shape of the skull 3. The fixation can be done by a screw 4 and/or by chemical fixation means, e.g. by gluing.

In its initial state, before the electrode 5 is fixated to the skull 3, as depicted in FIG. 8, the legs of the mechanical supporting structure 57 reach the outer circumference of the outmost lamellae 58. In this initial state, it is possible that the legs are only in mechanical contact with the outmost lamellae, but not with the inner ones.

In the course of fixating the electrode 5 to the skull 3, e.g. in an intermediate state depicted in FIG. 8a, the legs may get in contact with the inner lamellae 58. In the course of mounting the electrode to the skull 3, the bridging sections between inner and outer lamellae may be deformed, in particular they may be irreversibly deformed. This is helpful for maintaining the shape of the electrode adapted to the outer shape of the skull 3. In particular, the shape of the electrode is maintained also in case the legs are no longer in contact with at least some of the lamellae 58, as depicted in FIG. 9.

In addition, a silicone coating of the electrode 5 is also helpful for maintaining the adapted shape of the electrode, e.g. the shape depicted in FIG. 9, when the lamellae are snuggly adapted to the outer shape of the skull 3. In this situation, the mechanical supporting structure 57 may only exert some pressing force to the inner part of the electrode 5.

Figure 10:
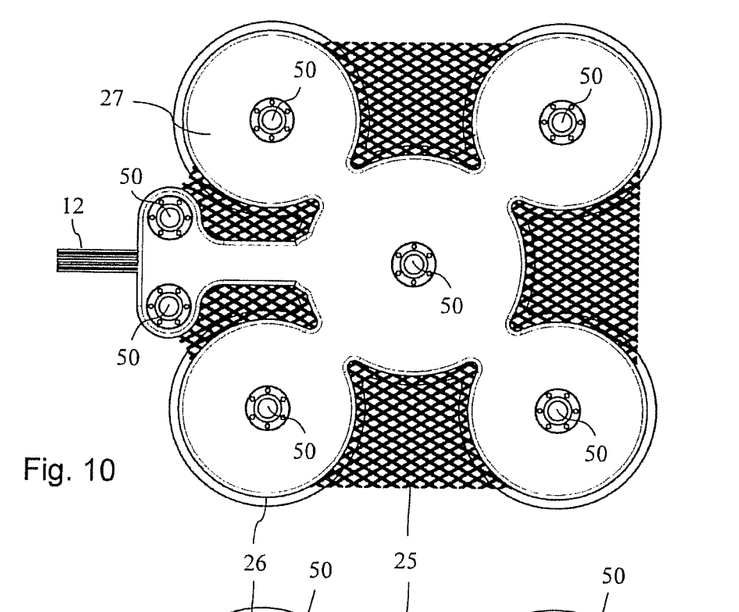
Figure 11:
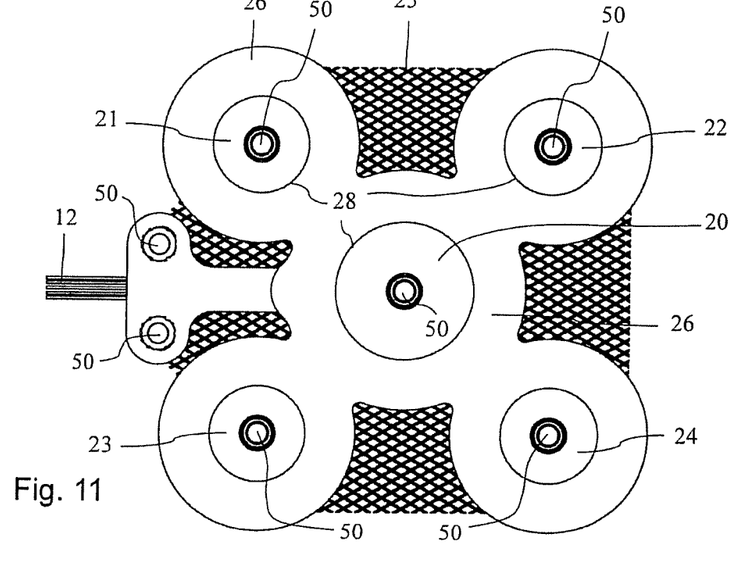

FIG. 10 shows an electrode pad 2 with electrodes of the aforementioned type in a plan view on the backside of the electrodes, FIG. 11 shows the electrode pad 2 of FIG. 10 with a plan view on the stimulation surface side. As can be seen, the electrodes are mechanically connected together by a surgical mesh 25 which may be covered at least partially by a flexible pad 26, for example a silicone pad.

As can be seen, the surgical mesh 25 is partially covered on the backside of the electrodes by a second flexible pad 27, for example another silicone pad. On the stimulation surface side, the electrodes are partially covered by the flexible pad 26, whereby on the transition from the material of the flexible pad 26 to the electrode an O-ring seal 28 can be formed by the material of the flexible pad 26. Further, it can be seen that there are several screw holes 50 for mounting the electrode pad 2 to the skull.

The invention claimed is:

1. An electrode for electrical stimulation of brain tissue or other tissue of a patient, the electrode being configured for location between skull and scalp of the patient, wherein the electrode has a stimulation surface which is configured for contacting the skull of the patient, wherein the electrode is a disc-shaped electrode having a pre-shaped stimulation surface, wherein the electrode comprises at least one cutting site in a form of one or more of an incision and a cut-out, allowing the electrode to be more flexibly deformable for adaption to an outer shape of the skull of the patient, wherein the at least one cutting site
      generally runs in a radial direction of the disc-shape of the electrode, and/or
      generally runs in a spiral form.

2. The electrode according to claim 1 wherein the cutting site
generally runs in a circumferential direction of the disc-shape of the electrode.

3. The electrode according to claim 1 wherein the electrode comprises multiple electrode arms divided by a plurality of cutting sites, wherein the electrode arms are joined at at least one joining surface of the electrode.

4. The electrode according to claim 1 wherein the cutting sites are without sharp edges.

5. The electrode according to claim 3 wherein the at least one joining surface is located in the center of the electrode.

6. The electrode according to claim 3 wherein at least some of the multiple electrode arms are supported by a mechanical supporting structure located on a backside of the electrode which is opposite the stimulation surface side.

7. The electrode according to claim 1 wherein the electrode comprises at least one mounting hole, allowing mounting of the electrode to the skull of the patient by means of a mechanical fixation element guided through the at least one mounting hole.

8. The electrode according to claim 1 wherein the electrode has a shape of a lily pad, an oxeye daisy flower and/or a terrace-like shape.

9. The electrode according to claim 1 wherein the electrode is at least partially coated with a flexible material.

10. The electrode according to claim 1 wherein the disc-shape of the electrode has a diameter that ranges from 10 to 20 millimeter.

11. An electrode pad for electrical stimulation of brain tissue or other tissue of a patient via electrodes located between skull and scalp of the patient, comprising one or more electrodes wherein the one or more electrodes are configured for location between the skull and the scalp of the patient, wherein the one or more electrodes have a stimulation surface which is configured for contacting the skull of the patient, wherein the one or more electrodes are disc-shaped having a pre-shaped stimulation surface, and
at least one cutting site in a form of one or more of an incision and a cut-out, allowing the electrode to be more flexibly deformable for adaption to an outer shape of the skull of the patient,
wherein the at least one cutting site
generally runs in a radial direction of the disc-shape of the electrode, and/or
generally runs in a spiral form.

12. The electrode pad according to claim 11 wherein leads for connecting the one or more electrodes to a stimulating device and/or connecting the one or more electrodes are preassembled on a surgical mesh.

13. The electrode pad according to claim 12 wherein the surgical mesh is partially or totally embedded within or covered by a flexible pad.

14. The electrode pad according to claim 11 further comprising at least one, stimulation electrode and at least one secondary electrode.

15. The electrode pad according to claim 14 wherein the at least one secondary electrode includes a plurality of secondary electrodes wherein at least one stimulation electrode is located between at least two of the plurality of secondary electrodes.

16. A method for electrical stimulation of brain tissue or other tissue of a patient, comprising using an electrode or electrode pad for electrical stimulation, the electrode being configured for location between skull and scalp of the patient, wherein the electrode has a stimulation surface which is configured for contacting the skull of the patient, wherein the electrode has at least one cutting site in a form of one or more of an incision and a cut-out, allowing the electrode to be more flexibly deformable for adaption to an outer shape of the skull of the patient,
wherein the at least one cutting site
generally runs in a radial direction of the disc-shape of the electrode, and/or
generally runs in a spiral form.

17. A method of applying an electrode or an electrode pad which includes the electrode to the skull of a patient, comprising locating the electrode between skull and scalp of the patient and fixing the electrode to the skull via a mechanical fixation element and/or by chemical fixation means, wherein the electrode has at least one cutting site in a form of one or more of an incision and a cut-out, allowing the electrode to be more flexibly deformable for adaption to an outer shape of the skull of the patient,
wherein the at least one cutting site
generally runs in a radial direction of the disc-shape of the electrode, and/or
generally runs in a spiral form.

18. The method according to claim 17 wherein the electrode is deformed when fixed to the skull from a pre-shaped form into a skull-specific form at a point of application.

* * * * *